(12) United States Patent
Mueller et al.

(10) Patent No.: US 10,481,093 B2
(45) Date of Patent: Nov. 19, 2019

(54) BEAM SPLITTER AND ARRANGEMENT FOR EXAMINING A SAMPLE WHICH CAN BE EXCITED BY MEANS OF ELECTROMAGNETIC RADIATION

(71) Applicant: EyeSense GmbH, Grossostheim (DE)

(72) Inventors: Ralf Mueller, Mittweida (DE); Hans-Georg Ortlepp, Apfelstaedt (DE)

(73) Assignee: EYESENSE GMBH, Grossosthe Im (DE)

( * ) Notice: Subject to any disclaimer, the term of this patent is extended or adjusted under 35 U.S.C. 154(b) by 0 days.

(21) Appl. No.: 15/550,325

(22) PCT Filed: Feb. 6, 2016

(86) PCT No.: PCT/EP2016/052581
§ 371 (c)(1),
(2) Date: Aug. 10, 2017

(87) PCT Pub. No.: WO2016/128334
PCT Pub. Date: Aug. 18, 2016

(65) Prior Publication Data
US 2018/0031475 A1     Feb. 1, 2018

(30) Foreign Application Priority Data
Feb. 10, 2015 (DE) .......... 10 2015 101 847

(51) Int. Cl.
*G01N 21/64* (2006.01)
*G02B 27/14* (2006.01)

(52) U.S. Cl.
CPC ......... *G01N 21/645* (2013.01); *G02B 27/141* (2013.01); *G02B 27/145* (2013.01);
(Continued)

(58) Field of Classification Search
CPC .......... G01N 21/645; G01N 2021/6471; G01N 2021/0846; G02B 27/141; G02B 27/145;
(Continued)

(56) References Cited

U.S. PATENT DOCUMENTS 3,659,918 A   5/1972   Tan
3,922,069 A   11/1975  Kishikawa et al.
(Continued)

FOREIGN PATENT DOCUMENTS

CN   203 930 052 U   11/2014
EP    1 856 509 B1    3/2006
(Continued)

OTHER PUBLICATIONS

English translation of International Preliminary Report on Patentability dated May 20, 2016 issued in connection with corresponding International Application No. PCT/EP2016/052581 (6 pages total).
(Continued)

*Primary Examiner* — David P Porta
*Assistant Examiner* — Blake C Riddick
(74) *Attorney, Agent, or Firm* — Mayer & Williams, PC; Stuart H. Mayer (57) ABSTRACT

An arrangement for examining a sample which can be excited by means of electromagnetic radiation comprises a first dichroitic beam splitter having a first and a second prism, which are connected to one another on the base surfaces thereof, and a dichroitic layer arranged between the base surfaces of the two prisms, wherein an entry surface of the first prism encloses an angle (β) in the range from 10° to <40° with the dichroitic layer. Furthermore a light source provides the electromagnetic radiation suitable for excitation of the sample, the radiation coupled into the entry surface of the first prism, wherein a part of the radiation is reflected on the dichroitic layer in the direction of the
(Continued)

sample, which is positioned downstream of an exit surface of the first prism. Finally, a detector detects electromagnetic radiation emitted by the sample, passed through the beam splitter and leaving the latter on a measurement surface. The invention further relates to a dichroitic beam splitter, for use in said arrangement.

16 Claims, 3 Drawing Sheets

(52) U.S. Cl.
CPC .............. *G01N 2021/6471* (2013.01); *G01N 2201/0846* (2013.01); *G02B 27/142* (2013.01)

(58) Field of Classification Search
CPC ... G02B 27/142; G02B 21/0008; G02B 21/16
USPC ............................... 250/458.1, 459.1, 492.1
See application file for complete search history.

(56) References Cited

U.S. PATENT DOCUMENTS

| | | | |
|---|---|---|---|
| 4,322,979 A * | 4/1982 | Fromm | G01L 9/0077 359/222.1 |
| 4,444,464 A | 4/1984 | Minott | |
| 4,969,730 A * | 11/1990 | van den Brandt | G02B 27/1026 348/E9.027 |
| 5,400,179 A | 3/1995 | Ito | |
| 5,572,353 A * | 11/1996 | Iizuka | G02B 26/105 359/205.1 |
| 5,668,664 A | 9/1997 | Shishido | |
| 5,828,497 A | 10/1998 | Neumann et al. | |
| 5,943,129 A * | 8/1999 | Hoyt | G01N 21/6456 250/458.1 |
| 6,912,300 B1 * | 6/2005 | Okamoto | G06K 9/00046 359/833 |
| 8,269,966 B2 | 9/2012 | Gruler | |
| 2001/0003490 A1 * | 6/2001 | Kawasaki | G02B 21/06 359/385 |
| 2002/0003612 A1 * | 1/2002 | Huang | G03B 21/14 353/81 |
| 2003/0197119 A1 * | 10/2003 | Engelhardt | G02B 21/002 250/234 |
| 2003/0198444 A1 * | 10/2003 | Mine | G02B 6/4246 385/89 |
| 2004/0075906 A1 * | 4/2004 | Sedlmayr | G02B 26/02 359/489.15 |
| 2008/0144028 A1 * | 6/2008 | Gruler | G01N 21/645 356/317 |
| 2009/0303317 A1 * | 12/2009 | Tesar | C03C 17/3417 348/65 |
| 2009/0323192 A1 * | 12/2009 | Towndrow | G02B 27/1013 359/634 |
| 2012/0008197 A1 * | 1/2012 | Borck | G02B 21/06 359/386 |
| 2012/0268573 A1 | 10/2012 | Schoenborn et al. | |
| 2013/0100443 A1 * | 4/2013 | Li | G02B 27/1006 356/317 |
| 2013/0308198 A1 | 11/2013 | Erdogan et al. | |
| 2014/0206580 A1 | 7/2014 | Grudzien et al. | |
| 2015/0048256 A1 * | 2/2015 | Matsumura | G01N 21/6452 250/453.11 |
| 2016/0306180 A1 * | 10/2016 | Rosa | G02B 27/1013 |

FOREIGN PATENT DOCUMENTS

| | | |
|---|---|---|
| EP | 2 711 762 A1 | 3/2014 |
| JP | 2006-275685 A | 10/2006 |
| JP | 2008-102352 A | 5/2008 |
| JP | 2009-31406 A1 | 3/2010 |
| JP | 2013-011257 A | 1/2013 |
| JP | 2013-185964 A | 9/2013 |
| WO | 2010/025536 A1 | 3/2010 |

OTHER PUBLICATIONS

English translation of International Search Report dated May 20, 2016 issued in connection with corresponding International Application No. PCT/EP2016/052581 (5 pages total).

Canadian Office Action dated Aug. 21, 2018, issued in connection with corresponding Canadian patent application No. 2,976,129 (4 pages total).

Japanese Office Action dated Nov. 14, 2018, issued in connection with corresponding Japanese patent application No. 2017-564135 with English language translation (6 pages total).

* cited by examiner

BEAM SPLITTER AND ARRANGEMENT FOR EXAMINING A SAMPLE WHICH CAN BE EXCITED BY MEANS OF ELECTROMAGNETIC RADIATION

FIELD

The present invention relates to a dichroic beam splitter, and an arrangement for examining a sample which can be excited by means of electromagnetic radiation. Dichroic beam splitters split incident light into certain wavelength ranges. The electromagnetic radiation considered here is light in the range between ultraviolet and infrared radiation.

BACKGROUND

A beam splitter is an optical component which splits a single beam into two partial beams. If a beam is incident on a beam splitter, then a portion of the incident beam is reflected and the other portion is transmitted. In the case of a dichroic beam splitter, depending on the wavelength of the incident beam, different transmission values or reflection values are obtained. Scattering losses are very small in the case of dichroic beam splitters, so that the degree of transmission plus the degree of reflection is nearly one.

Dichroic beam splitters are used for example in fluorescence meters, where they are usually configured as a dichroic beam splitter plate. Dichroic beam splitter plates have a dichroic coating on their surface. The surface normal of these plates is generally offset by 45° from the beam path. In the case of dichroic beam splitter plates the transmission characteristic over wavelength (transmission is a function of wavelength) includes a relatively steep transition edge of no to high transmission values, or vice versa.

As a result, dichroic beam splitter plates can find good use in the excitation of fluorescent materials, in which the excitation wavelength and the emission wavelength are relatively close together.

EP 1 856 509 B1 describes a fluorescence meter for examining a sample, comprising a main beam path and at least one optical module. The optical module is embodied so as to provide at least one electromagnetic beam for exciting the sample and receive at least one electromagnetic beam emitted by the sample. The fluorescence meter comprises at least one source for providing electromagnetic beams, which is monitored by means of a monitor diode. Preferably, several beam splitters which are configured as dichroic mirrors (dichroic beam splitter plates) are arranged in the main beam path. The dichroic mirrors or dichroic beam splitter plates can be regarded as high-pass filters which transmit longer wavelength electromagnetic beams and reflect shorter wavelength beams. They are optimized for an angle of incidence of the electromagnetic beam of 45°. By means of dichroic mirrors, for example, exciting electromagnetic beams of the source are coupled into the main beam path and focused on the sample.

From the prior art, beam splitter cubes are also known, which consist of two interconnected prisms, between which a dielectric layer is arranged. In EP 2 711 762 A1, a non-polarizing beam splitter cube is described, which has a sequence of layers of refractive layers of dielectric material with different refractive indices.

Non-polarizing beam splitter plates, as well as non-polarizing beam splitter cubes, split the incident light in a particular transmission/reflection ratio while maintaining the original polarization state. A dichroic function is not present here. All wavelengths are split in a particular ratio, e.g., 50% to 50%.

U.S. Pat. No. 5,400,179 A is concerned with a beam splitter consisting of two prisms, between which an optical layer of six sublayers is arranged. Adjacent sublayers have a different refractive index. The angle of incidence of a beam impinging on the optical layer is at least 40°. This publication does not address dichroic beam splitters. Rather, non-polarizing beam splitters are addressed. Such beam splitters can not be used, e.g., for fluorescence measurements since they do not have a transmission characteristic over the wavelength (transmission is a function of the wavelength) which has a transition edge of no to high transmission values, or vice versa.

JP 2009-31406 A shows a non-polarized beam splitter consisting of two prisms and a dielectric layer arranged between the two prisms consisting of several interconnected sublayers. The sublayers have different refractive indices. While at least one sublayer has a higher refractive index than the prisms, at least one other sublayer has a lower refractive index than the prisms. The beam splitter can consist of two prisms with a triangular or trapezoidal base surface. In the embodiments having a trapezoidal base surface, the angle of incidence of a beam impinging on the dielectric layer is substantially greater than 45°. In the exemplary embodiment described, the angle of incidence is 72°.

A beam splitter consisting of two trapezoidal prisms is known from WO 2010/025536 A1. Between the prisms there is a coating structure with an upper layer, a spacer layer and optionally a lower layer. The spacer layer encloses a cavity filled with non-reactive gas or vacuum which acts as an interference layer. The coating structure allows for thin film interference in conjunction with frustrated total reflection within the cavity for predetermined angles of incidence.

U.S. 2013/0308198 A1 discloses a dichroic beam splitter consisting of at least two interconnected prisms. The beam splitter has three outer surfaces arranged in different planes. Disposed in the beam splitter is a dichroic layer which crosses at least one of the surfaces.

Dichroic beam splitter cubes are also known from the prior art. Dichroic beam splitter cubes also split incident light into certain wavelength ranges. In the case of dichroic beam splitter cubes, too, depending on the wavelength of the incident beam, different transmission values or reflection values are obtained. Scatter losses are also very small in the case of dichroic beam splitter cubes, so that the degree of transmission plus the degree of reflection is nearly one. In the case of dichroic beam splitter cubes the transmission characteristic over the wavelength (transmission is a function of the wavelength) includes a relatively shallow transition edge from no to high transmission values, or vice versa. They are therefore not suitable for measurements in which the excitation wavelength and emission wavelength are relatively close together. This is the case, for example, in the measurement of fluorescent light, since for many fluorescent dyes the excitation wavelength and the emission wavelength are very close together. Typically, the excitation wavelength and the emission wavelength are separated by 20 to 30 nm, although a smaller separation is also possible. If the slope of the transmission characteristic is not steep enough, the transition range from high reflection to high transmission will extend clearly over a larger wavelength range than the 20 to 30 nm mentioned above. The excitation light would therefore falsify the measuring result. An advantage of beam splitter cubes is that further optical components can be arranged directly on the side surfaces of the beam splitter cube. This reduces the installation effort because the optical components can already be positioned correspondingly on the beam splitter cube.

An arrangement for the representation of micro-array data is described, for example, in U.S. 2014/0206580 A1. The arrangement comprises, inter alia, a dichroic mirror or a beam splitter. The beam splitter consists of two symmetrical, pentagonal beam splitter components. The beam splitter can be arranged with a central axis offset to the longitudinal axis of a support rod, on which the beam splitter is attached. The angle between the central axis of the beam splitter and the longitudinal axis of the support rod should be 30° to 45°. The angle between the entry surface for a laser radiation and the contact surface of the two beam splitter components is at a constant 45°.

A disadvantage of the previously known measuring arrangements, which are used in particular for the measurement of fluorescence, is that they have long reached the limits of miniaturizability and require a high adjustment effort. Dichroic beam splitter plates have above all the disadvantage that adjoining optical components must be adjusted freely in space and very precisely to these beam splitter plates. In the closer vicinity of beam splitters, however, often other optical elements are needed, such as light-absorbing arrangements. One possibility for light absorbing arrangements is to interleave interfaces between air and dark solid structures. Such light-absorbing arrangements can not be directly connected to beam splitter plates and are only insufficiently miniaturizable.

SUMMARY

The object of the present invention is to provide an arrangement for measuring radiation which is emitted by a sample and simultaneously exciting the sample with electromagnetic radiation, which can be easily miniaturized and installed and adjusted with little effort. Furthermore, a dichroic beam splitter for such an arrangement will be provided.

In order to achieve the object, an arrangement for examining a sample which can be excited by means of electromagnetic radiation is provided according to the appended claim 1, as well as a dichroic beam splitter according to the appended claim 10.

A dichroic beam splitter preferably used in the arrangement according to the invention comprises a first and a second prism, which are connected to one another on the base surfaces thereof, and a dichroic layer or dichroic coating arranged between the base surfaces of the two prisms, wherein an entry surface of the first prism is preferably perpendicular to incident radiation. This means that the surface normal of the entry surface preferably runs parallel to the incident radiation. Even after beam shaping, many beam sources have an angle-radiation characteristic. The beam source is thus preferably oriented such that the direction of the greatest beam intensity is parallel to the surface normal of the entry surface. The entry surface of the first prism encloses an angle in the range of 10° to <40° with the dichroic layer, with an angle in the range of 25° to 35° being found to be particularly favorable. This results in an angle of incidence in the range from 10° to <40° to the surface normal of the dichroic layer for a radiation impinging on the dichroic layer.

A substantial advantage of the solution according to the invention is seen in the fact that, due to the specific geometric configuration of the prisms, a beam splitter is provided whose transmission characteristic over the wavelength (transmission is a function of the wavelength) in the transition area between low and high transmission has a similar steep profile as the transmission characteristic over the wavelength (transmission is a function of the wavelength) in the transition area between low and high transmission of the previously known dichroic beam splitter plates. This is achieved by the angle of incidence realized according to the invention on the dichroic layer.

In contrast to the configuration according to the invention, in the case of known non-polarizing dichroic beam splitter plates, the light is refracted by air into the dichroic layer. For beam splitter plates, the angle of incidence is generally 45° to the surface normal of the dichroic layer. If the first sublayer of the dichroic layer has, for example, a refractive index of 1.7, then the angle of the radiation to the surface normal of the dichroic layer within the first sublayer is approximately 24.6° (by refraction). This relatively small angle continues to propagate further in further sublayers of the dichroic layer and is the reason why the transition area of high transmission (e.g. 95%) to low transmission (e.g. 0.2%) can be effected within 20 to 30 nm.

In conventional non-polarizing dichroic beam splitter cubes, the light is refracted by a dielectric material (e.g., glass; refractive index approx. 1.5) into the first sublayer of the dichroic layer. For a cube, the angle of incidence is 45° to the surface normal of the dichroic layer. If the first sublayer of the dichroic layer again has a refractive index of 1.7, for example, then the angle of the radiation to the surface normal of the dichroic layer within the first sublayer is approx. 38.6° (by refraction). This relatively large angle continues to propagate further in further sublayers of the dichroic layer, and is the reason why the transition area of high transmission (e.g. 90%) to low transmission (e.g. 10%) can be effected only within 300 to 400 nm. This can, in turn, be attributed to the fact that at this relatively large angle, increasingly more total reflections take place between the individual sublayers of the dichroic layer.

In comparison to the dichroic plate, the beam splitter according to the invention furthermore has the advantage that additional optical elements can be attached directly, for example via an adhesive connection, to the outer surfaces of the beam splitter. This is very useful since the optical elements are thus already adjusted in their distance and their angle to the dichroic layer. Thus, a predetermined distance of the optical elements is exactly maintained. In this way, the adjustment effort is shifted into the manufacturing process of the prisms, in which high-precision production processes are used in any case. According to the invention, a self-supporting structure is created which does not require an additional housing.

In an advantageous embodiment, an exit surface of the first prism encloses an angle in the range from 10 to <40° with the dichroic layer, wherein the exit surface of the first prism is perpendicular to an exiting radiation.

According to a preferred embodiment, the dichroic layer or dichroic coating consists of dielectric material. The dichroic layer can consist of several sublayers of dielectric material with different refractive indices. Common materials are, for example, $TiO_2$, $AlF_3$, $Al_2O_3$. When using low-refractive-index materials, the refractive index can be, for example, in the range from 1.3 to 1.5. In the case of medium-refractive-index materials, the refractive index is, for example, >1.5 to 1.8. High-refractive-index materials can have a refractive index >1.8 to 2.4.

Configuring a beam splitter with a base surface in the form of a regular hexagon has proved to be advantageous. However, it is not intended to be limited to a beam splitter configured in this way, other configurations are quite possible. In the case of beam splitters with a hexagonal base area there are relatively many areas available for attaching additional optical elements.

The beam splitter preferably consists of two prisms of the same type, although embodiments with prisms of different types are also possible. The possible shaping of the prisms is limited only by the fact that the angle required according to the invention between the entry surface of one of the two prisms and the dichroic layer falls in the range from 10° to <40°. The two prisms preferably have the same refractive index.

The arrangement according to the invention for examining a sample which can be excited by means of electromagnetic radiation comprises firstly a light source for providing an electromagnetic radiation serving to excite the sample. The light source can, for example, be an LED or a laser, and, in modified embodiments, also devices for beam shaping, such as, for example, lenses and apertures. A further component of the arrangement is the dichroic beam splitter described above comprising a first and a second prism which are connected to one another on the base surfaces thereof, and a dichroic layer arranged between the base surfaces of the two prisms. The dichroic beam splitter serves to deflect at least a portion of the electromagnetic radiation provided by the light source in the direction of the sample and to pass through an electromagnetic radiation emitted by the sample after its excitation. The arrangement also includes a detector for detecting the electromagnetic radiation emitted by the sample. The detector can be configured as a photodiode.

According to a preferred embodiment, the arrangement comprises one or more further optical components, which are attached to the outer surfaces of the beam splitter. The optical components are preferably fixed on the outer surfaces of the beam splitter by means of a suitable adhesive. The optical components in question include, for example, filters, lenses, beam deflectors, detector elements, such as, e.g. photodiodes or absorbers.

Filters are used, for example, for filtering out certain frequency ranges of the radiation emitted by the light source. Thus, the sample can be excited at a suitable frequency. For this purpose, the filter must be attached to the beam splitter in such a way that the radiation emitted by the light source passes through the filter before it enters the beam splitter.

For example, a lens can be positioned on the beam splitter in such a way that the radiation reflected by the dichroic layer of the beam splitter or the radiation emitted by the sample passes through the lens on its path to or from the sample and aligns it accordingly. In a specific exemplary embodiment, a lens is used to couple electromagnetic radiation into and also out of a light-guiding fiber.

In an advantageous embodiment, the light-guiding fiber is firmly connected to the sample. In an alternative embodiment, the light-guiding fiber is not firmly connected to the sample, the light guiding fiber can, for example, project into a larger sample.

In a further embodiment, a beam deflection unit is used as the optical component. The beam deflection unit is preferably attached on the outside of the exit surface of the first prism and is particularly preferably made of plastic or glass, for example as an injection-molded part made of plastic or an embossing member made of glass. The beam deflecting unit preferably has an angled tubular shape. The beam deflection unit serves the deflection of the electromagnetic radiation (light). The beam deflection preferably takes place at a 90° angle, the deflection surface preferably being located opposite the exit surface of the first prism. In order to realize a 90° deflection, an optical surface and the exit surface of the first prism span an angle of 45°. For the deflection, the beam deflection unit preferably has at least one optical surface, on which the beam path undergoes a total reflection.

In a modified embodiment, it is possible that a first optical surface realizes the deflection and also takes over a part of the coupling into the fiber. For this purpose, the first optical surface can be a toric surface. In addition, the first optical surface can be aspherical in one of its cross-sections. A second optical surface is then generally rotationally symmetrical and can be both spherical and aspherical.

The first optical surface can be formed on a glass body or a metallized surface and can be realized as a deflection mirror or a toroidal mirror.

In a further embodiment, the deflected radiation is coupled into or out of the light-guiding fiber. The light-guiding fiber is arranged perpendicular to the beam splitter by the beam deflecting unit, whereby an advantageous structure of the arrangement is realized.

The arrangement of an absorber on a surface of the beam splitter, which is arranged opposite the entry surface of the beam splitter has proved to be advantageous, through which the radiation emitted by the light source enters into the beam splitter. The fraction of the radiation emitted by the light source which is transmitted by the beam splitter can be absorbed by means of absorbers so that this fraction does not reach the detector in an uncontrolled manner, e.g., by light scattering effects. Only electromagnetic radiation emitted (non-reflected) from the sample may reach the detector.

According to a further modified embodiment, a further beam splitter can also be used as a further optical component, preferably a second dichroic splitter beam configured in the way described above. The functionality of the dichroic layer (position of the edge) of the second beam splitter can, of course, be configured differently compared to that of the first beam splitter. Thus, two of these novel beam splitter cubes are assembled. In the second beam splitter cube, for example, the fluorescence radiation emitted by the sample is then split in two wavelengths.

The arrangement according to the invention is preferably used for the measurement of radiation occurring upon excitation of fluorescent samples. However, there is no limitation to fluorescence measurements.

BRIEF DESCRIPTION OF THE DRAWINGS

Further advantages and details of the invention will become apparent from the following description of preferred embodiments with reference to the accompanying drawing.

DETAILED DESCRIPTION

Figure 1:
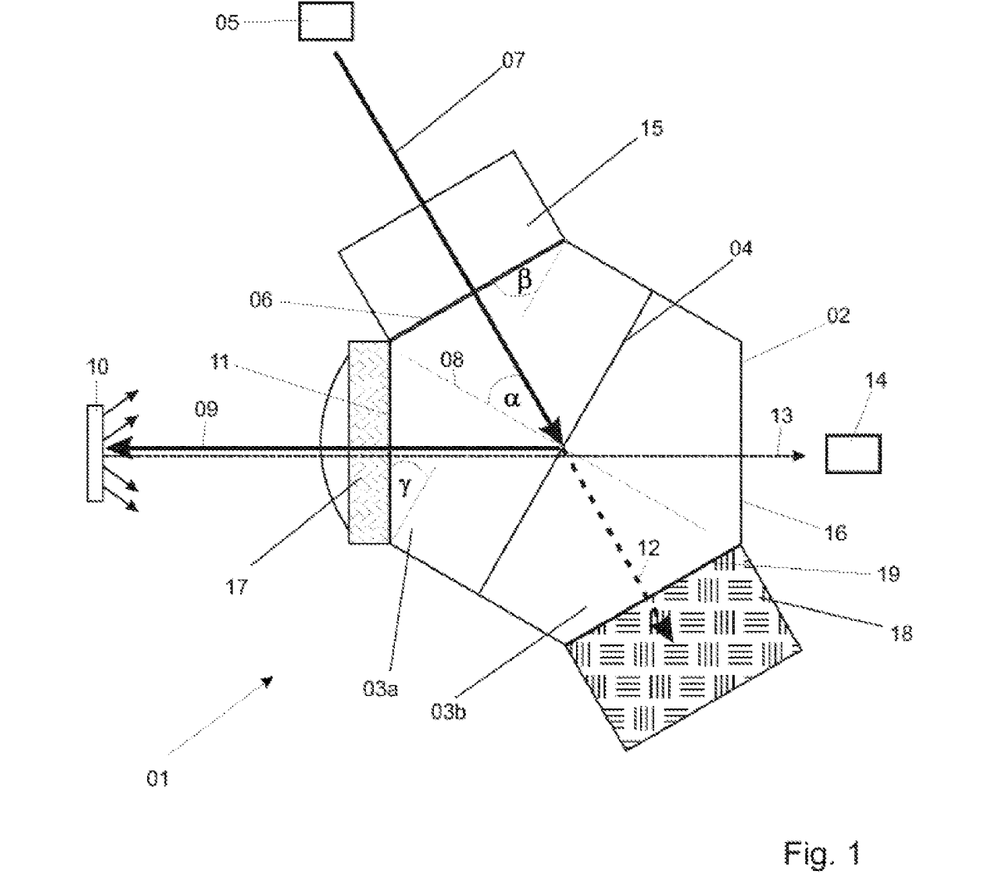
FIG. 1 shows an arrangement according to the invention for examining a sample which can be excited by means of electromagnetic radiation.

An arrangement 01 according to the invention shown in FIG. 1 includes a dichroic beam splitter 02, which consists of two prisms 03 which are connected to one another. In the configuration show, a first prism 03a and a second prism 03b are of the same type. However, embodiments are also possible in which differently configured prisms 03 are used.

Between the prisms 03 there is a dichroic layer 04. The dichroic layer 04 is preferably formed as a coating on one of the opposite base surfaces of the prisms 03 which are connected to one another. Likewise, both prisms 03 can also have a coating on their base surface. The dichroic layer 04 may consist of several sublayers of dielectric material with different refractive indices. The prisms 03 have a pentagonal base surface in the configuration shown. This results in a base surface in the form of a regular hexagon for the beam splitter 02 composed of the two prisms 03. However, there is no limitation to hexagonal beam splitters 02. The configuration of the prisms 03 and the associated arrangement of the dichroic layer 04 should merely ensure that a beam impinging on dichroic layer 04 has an angle of incidence in the range from 10° to <40° to the surface normal to the normal 08 of the dichroic layer 04.

The arrangement also includes a light source 05, which may also include devices for beam shaping, which emits an electromagnetic radiation 07, preferably in a collimated form. Light source 05 and beam splitter 02 are arranged in such a way that the radiation 07 emitted by the light source 05 is incident centrally and perpendicularly on an entry surface 06 of the first prism 03a. However, there is no limitation to the perpendicular and/or central incidence of light. In the embodiment shown, the entry surface 06 and the dichroic layer 04 enclose an angle β of about 30°. For the angle of incidence α, measured to the surface normal 08 of the dichroic layer, of the radiation 07 impinging on the dichroic layer 04 this also amounts to about 30°. Of the radiation 07 impinging on the dichroic layer 04, a partial radiation 09 is reflected in the direction of a sample 10 and a partial radiation 12 is transmitted. The dichroic layer 04 is configured in such a way that the fractions of the radiation 07, which are suitable for excitation of the sample 10, are reflected on the dichroic layer 04 and exit from the beam splitter 02 at an exit surface 11 of the first prism 03a. The angle γ enclosed by the exit surface 11 of the first prism 03a and the dichroic layer 04 is also 30° in the embodiment shown. An angle of 120° thus spans the entry surface 06 and the exit surface 11.

Upon impinging of partial radiation 09, the sample 10 emits a radiation 13 which is reflected back into the beam splitter 02 via the exit surface 11 of the first prism 03a, transmitted through the dichroic layer 04, and then leaves the beam splitter 02 on the opposite side, namely on a measurement surface 16 of the second prism 03b. The measurement surface 16 of the second prism 03b and the exit surface 11 of the first prism 03a are arranged in parallel opposite one another, but are located on different sides with respect to the dichroic layer 04. This emitted radiation 13 is detected by means of a correspondingly arranged detector 14. The detector 14 can be arranged at a distance from the measurement surface 16 or can also be attached directly thereto. A further deflection of the radiation via mirrors is also possible.

Further optical components are arranged on the outer surfaces of the beam splitter 02, which are preferably fixed to the outer surfaces by means of adhesive. Thus, a filter 15 is located directly on the entry surface 06 in the beam path of the radiation 07 emitted by the light source 05. Certain frequency ranges of the radiation 07 can be filtered out by the filter 15 in order to allow essentially the frequency ranges of the radiation 07 suitable for excitation of the sample 10 to pass through. A lens 17 is arranged on the exit surface 11 of the beam splitter 02 directed toward the sample 10, which lens bundles the radiation 13 emitted by the sample 10 after its excitation, in order to direct it toward the detector 14. An absorber 18 is arranged on an absorber surface 19 of the beam splitter 02 which is located opposite the entry surface 06, through which the radiation 07 emitted by the light source 05 enters into the beam splitter 02. The entry surface 06 and the absorber surface 19 are parallel to one another, but on different sides with respect to the dichroic layer 04. The absorber 18 absorbs the partial radiation 12 transmitted at the dichroic layer 04. The absorber surface 19 and the measurement surface 16 span an angle of 120° when the two prisms 03a, 03b are of the same shape and the angle α between the incident radiation 07 and the surface normal of the dichroic surface is 30°.

The arrangement 01 according to the invention can, in particular, be employed for fluorescence measurement without being limited to this particular application. Implementing an angle of incidence α of about 30° of the radiation 07 impinging on the dichroic layer 04, provides, in accordance with the invention, a beam splitter 02 having a transmission characteristic over the wavelength (transmission is a function of the wavelength), which is relatively steep in the transition area between low and high transmission. Relatively steep means that the transition area of high transmission (e.g. 95%) to low transmission (e.g. 0.2%) can be effected within 10 to 30 nm. Thus, there is no risk that fractions of the radiation 07 serving for the excitation will falsify the measuring result. Furthermore, there is no risk that the emitted radiation (13) will not be sufficiently transmitted at the dichroic layer (04).

Figure 2:
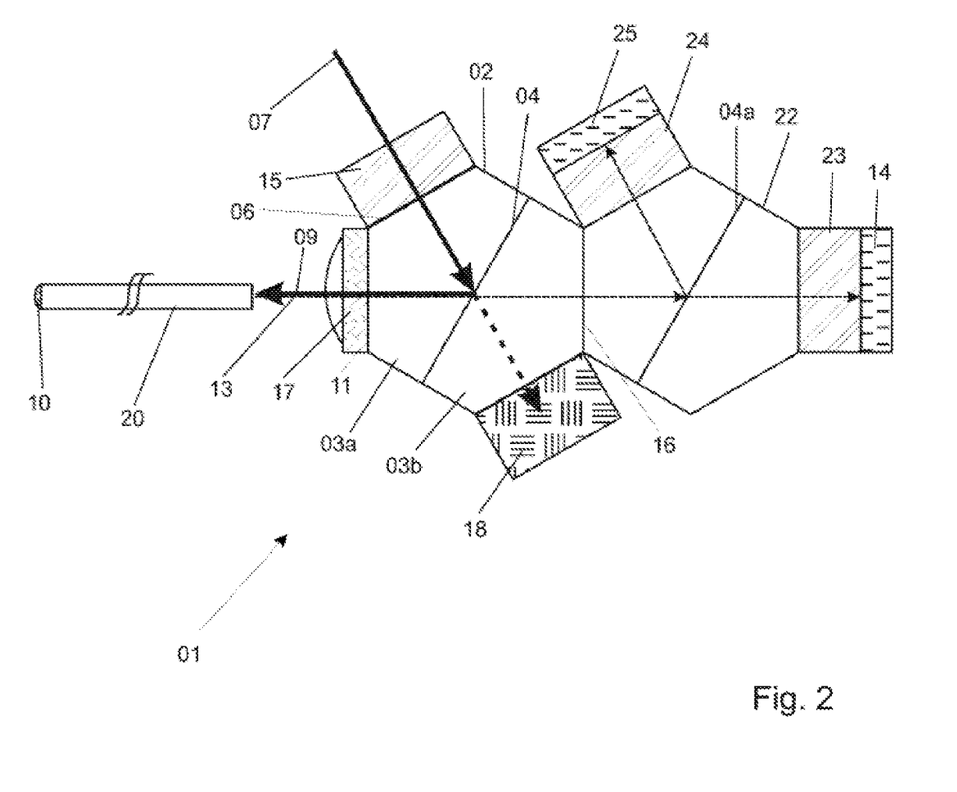
FIG. 2 shows a modified embodiment of the arrangement suitable for measuring glucose concentrations.

FIG. 2 shows a modified embodiment of the arrangement 01 according to the invention. It is used for examining a substance which is suitable for a fluorometric measurement of glucose concentrations.

To this end, the arrangement comprises the first beam splitter 02, the first filter 15 affixed thereto, the absorber 18 as well as the lens 17 which couples the partial radiation 09 reflected at the dichroic layer 04 into a light-guiding optical fiber 20. The sample 10, which in this case is a substance which changes its fluorometric properties as a function of the glucose concentration surrounding it, is arranged at the remote end of the optical fiber 20. For this purpose, this substance is configured in such a way that the intensity of a first emission wavelength range depends on the glucose concentration and the intensity of a second emission wavelength range does not depend on the glucose concentration and serves as a reference. The light emitted from this substance is coupled back into the first beam splitter 02 as the emitted radiation 13. The emitted radiation 13 passes through the first beam splitter 02 in the manner described and is now coupled into a second beam splitter 22 on the measurement surface 16. The second beam splitter 22 thus forms an optical component which can be attached directly to the first beam splitter 02. The emitted radiation 13 impinges on a second dichroic layer 04a in the second beam splitter 22, where the two wavelength ranges are split. The portion of the emitted radiation 13 transmitted on the second dichroic layer 04a therefore reaches the first detector 14 via a second filter 23, while the reflected part reached a second detector 25 through a third filter 24.

Figure 3:
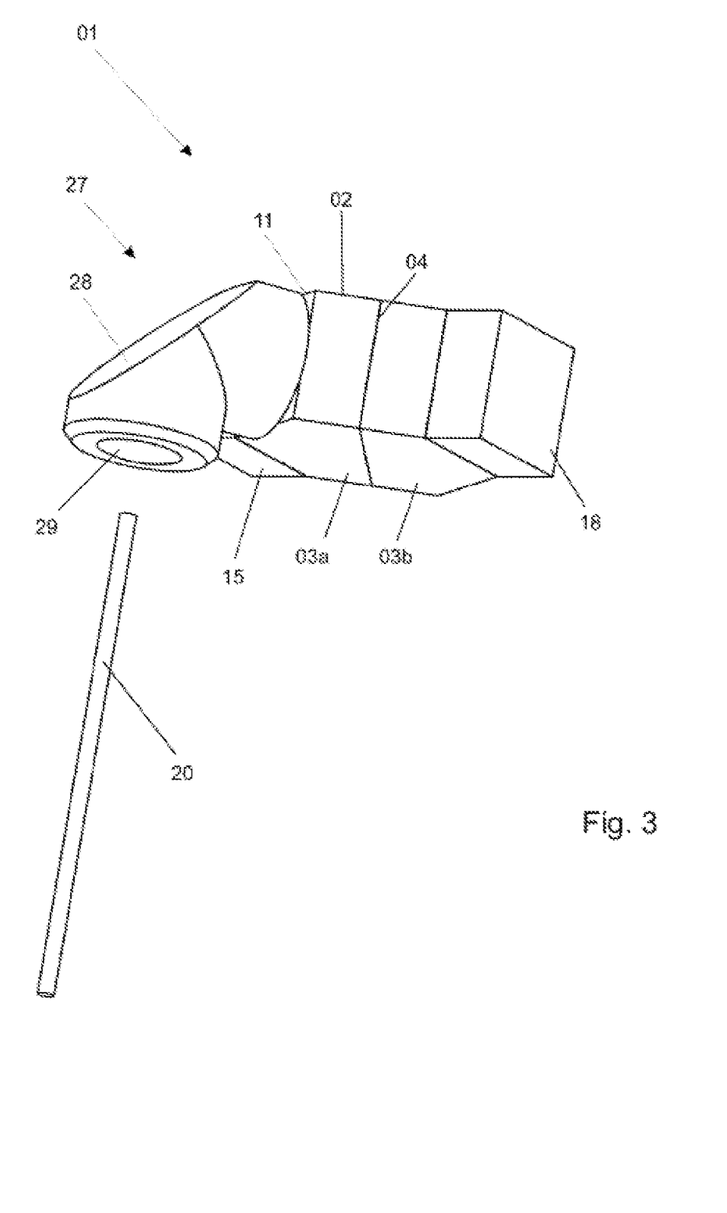
FIG. 3 shows details of a modified embodiment of the arrangement for examining a sample which can be excited by means of electromagnetic radiation.

FIG. 3 shows some elements of a modified embodiment of the arrangement 01 according to the invention, which is intended for examining a sample which can be excited by means of electromagnetic radiation. The basic structure of this embodiment is similar to that of the embodiments described above. The embodiment shown in FIG. 3 has only one beam splitter 02. In contrast to the embodiments shown in FIGS. 1 and 2, instead of the lens, a beam deflection unit 27 is affixed on the exit surface 11 of the first prism 03a. In the area opposite the exit surface 11, the tubular beam deflecting unit 27 is angled downwards by 90° in the direction towards the sample (not shown) to be arranged there. The area opposite the exit surface 11 is flattened so that an angle of 45° spans this area and the exit surface 11. The area opposite the exit surface 11 forms a first optical surface 28 which effects a 90° deflection of the reflected partial radiation or of the radiation emitted by the sample. On a second optical surface 29, which is located at the free end of the tubular beam deflecting unit 27, the reflected partial radiation exits or the emitted radiation 13 enters into this surface. The second optical surface 29 has a spherical surface, thereby focusing the radiation. This serves, in particular, for coupling the radiation into the optical fiber 20. The focusing is assisted by the first optical surface 28 when it has a toric shape. In this case, the optical fiber 20 runs perpendicular to the beam splitter 02, whereby an overall flat structure of the arrangement 01 is made possible.

LIST OF REFERENCE NUMERALS

01—arrangement
02—first beam splitter
03—prisms
04—dichroic layer
05—light source
06—entry surface
07—electromagnetic radiation
08—surface normal of the dichroic layer
09—reflected partial radiation
10—sample
11—exit surface
12—transmitted partial radiation
13—emitted radiation
14—first detector
15—filter
16—measurement surface
17—lens
18—absorber
19—absorber surface
20—optical fiber
22—second beam splitter
23—second filter
24—third filter
25—second detector
27—beam deflection unit
28—first optical surface
29—second optical surface
α—angle of incidence
β—angle between entry surface 06 and layer 04
γ—angle between exit surface 11 and layer 04

The invention claimed is:

1. An arrangement for examining a sample which can be excited by means of electromagnetic radiation, comprising:
   a first dichroic beam splitter comprising a first prism and a second prism connected to one another on base surfaces thereof, and a dichroic layer arranged between the base surfaces of the first and second prisms, wherein an entry surface of the first prism and the dichroic layer form an angle (β) in the range from 10° to <40°;
   a light source for providing electromagnetic radiation suitable for excitation of the sample, wherein the electromagnetic radiation is coupled into the entry surface of the first prism and wherein at least a part of the electromagnetic radiation from the light source is reflected on the dichroic layer in the direction of the sample, which is positioned downstream of an exit surface of the first prism; and
   a detector for detecting electromagnetic radiation emitted by the sample upon impinging of the at least part of the electromagnetic radiation, the emitted electromagnetic radiation passing through the first dichroic beam splitter without being reflected and onto a measurement surface of the second prism.

2. The arrangement according to claim 1, wherein the measurement surface of the second prism is arranged in parallel opposite of the exit surface.

3. The arrangement according to claim 1 further comprising at least one further optical component attached to an outer surface of the first dichroic beam splitter.

4. The arrangement according to claim 3, wherein the optical component is selected from the group consisting of:
   a lens,
   a filter,
   an absorber,
   a beam deflecting unit, or
   a second dichroic beam splitter which corresponds in its construction to the first dichroic beam splitter.

5. The arrangement according to claim 4, wherein a beam deflecting unit is attached to the exit surface and has at least one first optical surface which deflects the radiation reflected at the dichroic layer and exiting at the exit surface to an optical fiber.

6. The arrangement according to claim 5, wherein the first optical surface has a toric shape.

7. The arrangement according to claim 5, wherein the beam deflecting unit deflects the electromagnetic radiation by 90°.

8. The arrangement according to claim 4, wherein the beam deflecting unit consists of glass or plastic.

9. The arrangement according to claim 1, wherein a lens is attached to the exit surface of the first prism, wherein said lens couples radiation reflected at the dichroic layer into an optical fiber, and wherein the sample is positioned at a remote end of the optical fiber.

10. The arrangement according to claim 1,
    wherein the reflected partial electromagnetic radiation is reflected on the dichroic layer in the direction of an exit surface of the first prism and a transmitted partial radiation is transmitted through the dichroic layer.

11. A dichroic beam splitter, comprising:
    a first prism and a second prism which are connected to one another on base surfaces thereof, and
    a dichroic layer arranged between the base surfaces of the first prism and the second prism,
       wherein an entry surface of the first prism, on which radiation is incident, and the dichroic layer form forms-an angle (β) in the range of 25° to 35° wherein an exit surface of the first prism and the dichroic layer form an angle (γ) in the range of 25° to 35°, so that a reflected partial radiation is reflected on the dichroic layer in the direction of the exit surface of the first prism toward a sample, and a transmitted partial radiation emitted by the sample is transmitted through the dichroic layer-and wherein the beam splitter has a base surface in the form of a regular hexagon.

12. The dichroic beam splitter according to claim 11, wherein the dichroic layer consists of dielectric material.

13. The dichroic beam splitter according to claim 11, wherein the first prism and the second prism are of the same type.

14. An arrangement for examining a sample which can be excited by means of electromagnetic radiation, comprising:
- a first dichroic beam splitter comprising a first prism and a second prism connected to one another on base surfaces thereof, and a first dichroic layer arranged between the base surfaces of the first and second prisms, wherein an entry surface of the first prism forms an angle (β) in the range from 10° to <40° with the first dichroic layer;
- a second dichroic beam splitter comprising a third prism and a fourth prism connected to one another on base surfaces thereof, and a second dichroic layer arranged between the base surfaces of the third and fourth prisms, wherein an entry surface of the third prism forms an angle (β) in the range from 10° to <40° with the second dichroic layer;
- a light source for providing electromagnetic radiation suitable for excitation of the sample, wherein the electromagnetic radiation is coupled into the entry surface of the first prism and wherein at least a part of the electromagnetic radiation from the light source is reflected on the first dichroic layer in the direction of the sample, which is positioned downstream of an exit surface of the first prism; and
- a first detector for detecting electromagnetic radiation emitted by the sample, the emitted radiation passing through the first dichroic beam splitter, onto a measurement surface of the second prism, impinging upon the second dichoric layer, and at least a portion of the emitted radiation is transmitted through the second dichroic layer to the detector.

15. The arrangement according to claim 14, wherein a part of the emitted radiation that impinges on the second dichroic layer is reflected to a second detector.

16. The arrangement according to claim 15, wherein the reflected part of the emitted radiation reaches the second detector through a filter.

* * * * *